United States Patent [19]
van den Burg

[11] Patent Number: 5,003,828
[45] Date of Patent: Apr. 2, 1991

[54] FLOWMETER FOR GASES

[75] Inventor: Johannes M. E. van den Burg, Houten, Netherlands

[73] Assignee: Mijnhardt B.V., Bunnik, Netherlands

[21] Appl. No.: 436,375

[22] Filed: Nov. 14, 1989

[30] Foreign Application Priority Data

Nov. 15, 1988 [NL] Netherlands ................. 8802809

[51] Int. Cl.$^5$ ............................... G01F 1/10
[52] U.S. Cl. ..................... 73/861.33; 73/861.77; 73/861.89; 128/726
[58] Field of Search ........... 73/861.33, 861.77, 861.89, 73/861.92; 128/726

[56] References Cited

U.S. PATENT DOCUMENTS

| | | | |
|---|---|---|---|
| 2,934,947 | 5/1960 | Buck | 73/861.89 |
| 3,240,063 | 3/1966 | Brueckner | . |
| 3,792,611 | 2/1974 | Kozak | . |
| 3,922,525 | 11/1975 | Kozak | . |

OTHER PUBLICATIONS

Biomedizinische Technik, vol. 21, No. 8, 1976, pp. 228-230 (Schneiderreit).

Primary Examiner—Herbert Goldstein
Attorney, Agent, or Firm—Michael N. Meller

[57] ABSTRACT

A flowmeter for gases has a rotor between two stators which consist of deflection blades, and an otpical system for detecting the rotation of the rotor and converting it into an electrical output signal. Each of the detector blades of the stators has a curved course between an inflow edge, where the blade from the hub to the periphery runs substantially in an axial plane, and an outflow edge, where the blade surface at each point thereof forms an angle with the axial direction which angle varies with the distance of each point from the hub. Preferably the blade face is at least partially formed by a circular cylindrical face, the central axis of the cylinder and the central axis of the stator being at an angle differing from 90 and the central axis of the stator lying in a tangent plane to the cylinder, and a flat face part, lying in an axial plane, connects the circular cylindrical part of the stator face to the inflow edge, the axial measurement of the flat face part decreasing from the hub to the peripheral edge.

11 Claims, 4 Drawing Sheets

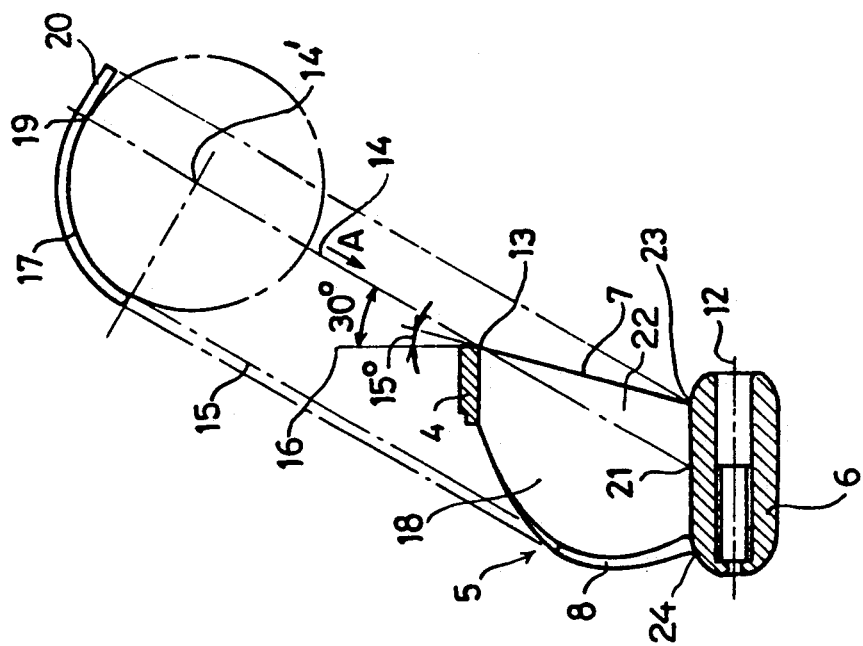
_Fig. 3._
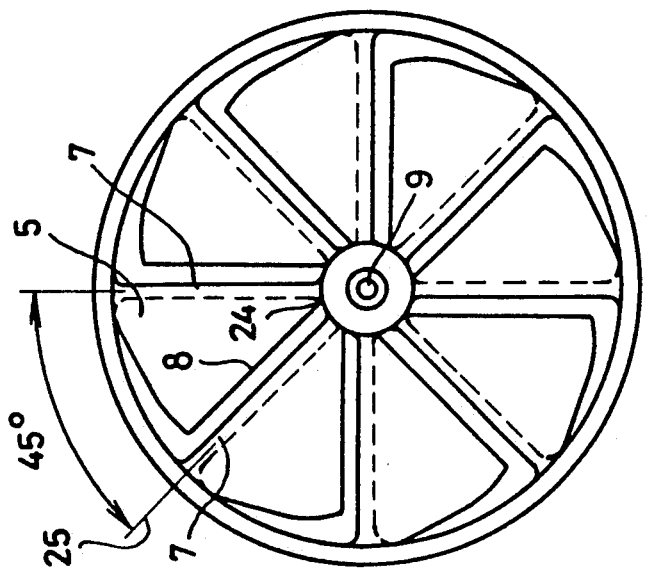
_Fig. 4._
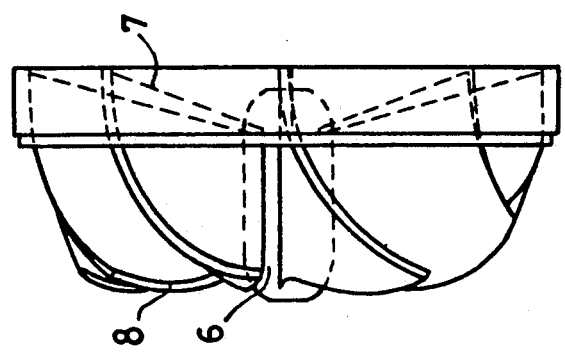
_Fig. 5._

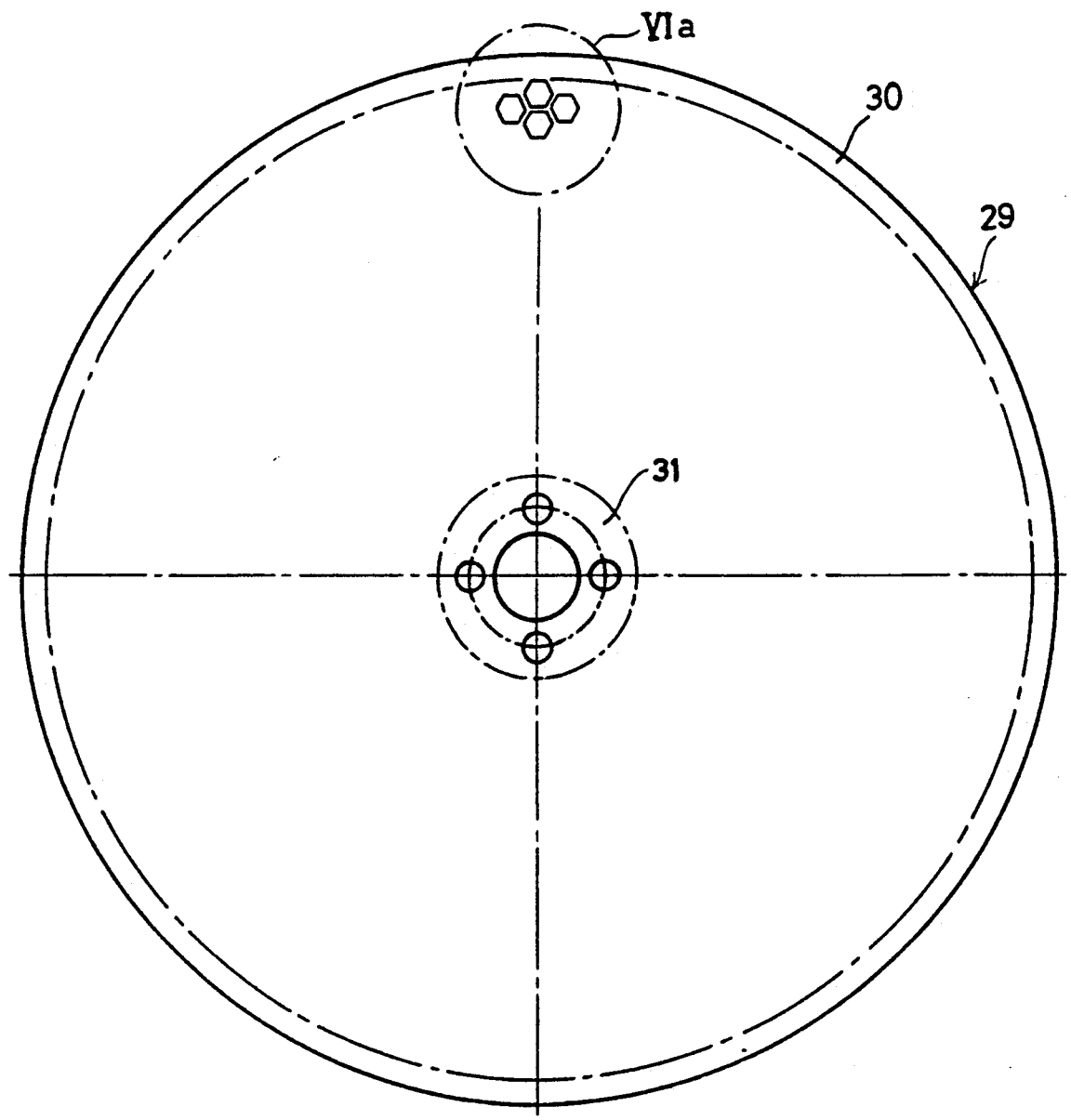
FIG:6.
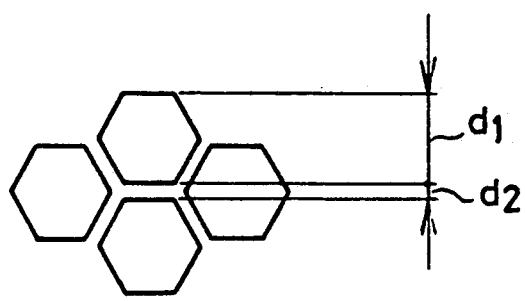
FIG:6a.

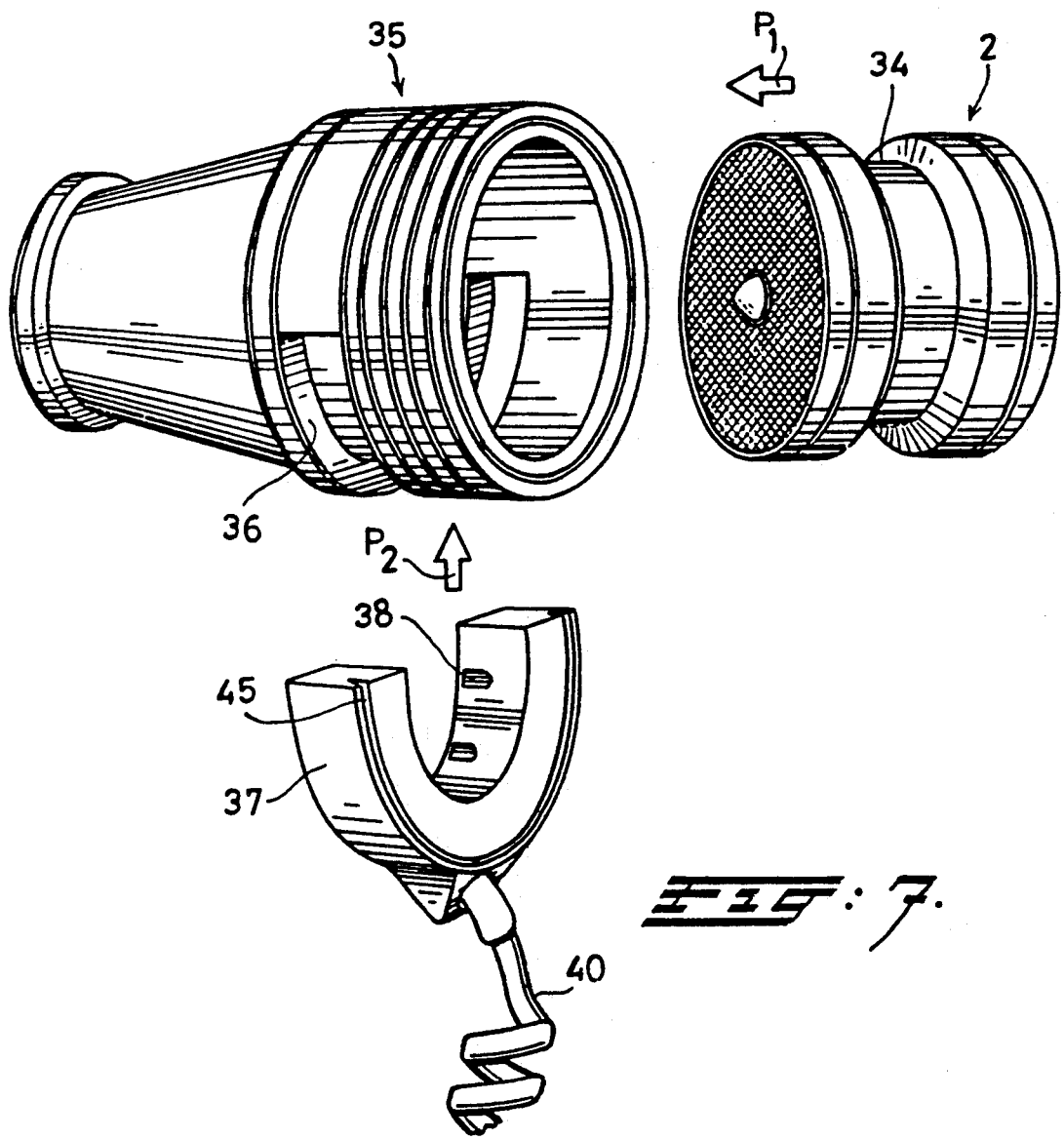
FIG: 7.
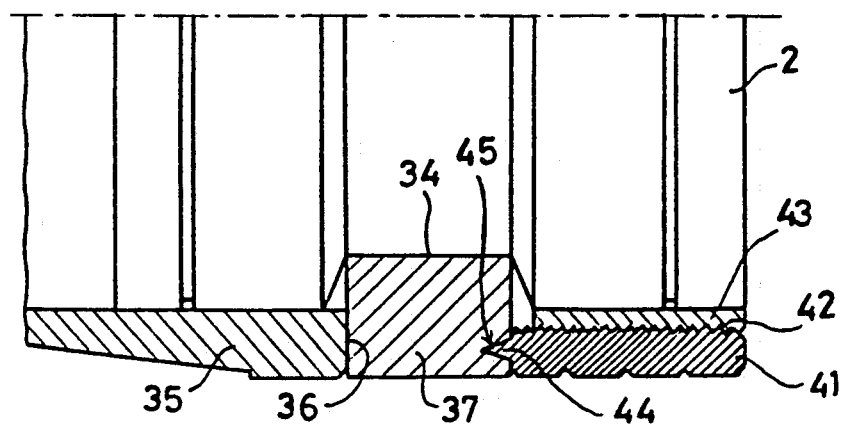
FIG: 8.

FLOWMETER FOR GASES

BACKGROUND OF THE INVENTION

State of the Art

The invention relates to a flowmeter for gases, the sensor of which has a housing which is open at two opposite ends for the infeed and discharge of the gases to be measured, and in which a rotor is rotatable about an axis between two stators which consist of deflection blades which are substantially at right angles to the axis, while optical means are arranged to detect the rotation of the rotor and convert it into an electrical output signal.

Such a flowmeter has been used by applicants, in particular in various instruments for measuring and analyzing breathing gases. The sensor has a housing which is circular cylindrical. The stators are formed by a metal disc in which are set a number of blades which are flat per se, and which all lie at an angle relative to axial faces. This slanting position is necessary to ensure that axially inflowing gases can be converted into a vortex which is capable of setting the rotor in rotation, the rotor being designed as a small vane which lies in an axial plane with an axis of rotation corresponding to the central axis of the sensor. As a result of the sudden deflection undergone by the inflowing gases, a flow pattern whose type depends to a large extent on the absolute value of the rate of flow of the gases, is produced.

It is possible to eliminate the consequences of this through calibration, but the problem then encountered is that the individual sensors doe not have any reproducible features. They are not even bidirectional. Each instrument thus has to be calibrated separately, and the sensor may be placed in only one specific position. It is thus not possible to compensate for the non-linearities in the features by means of a hardware or software, because it is necessarily identical for all instruments.

These problems are caused by the fact that for the known sensor there is no method of production other than by manual labor, whereby the blades are fixed individually relative to the little disc forming the center piece of each stator, while everything is moreover glued by hand in the cylindrical housing.

THE OBJECTS OF THE INVENTION

The prime object of the invention is to improve the above-mentioned device in various respects and to produce a flowmeter with better reproducibility of the features between the individual units and in the two positions.

Another object is that this is achieved in such a way that the instrument has a very great dynamic range.

SUMMARY OF THE INVENTION

In the basic idea the flowmeter according to the invention is characterized in that each of the stator blades has a curved course between an inflow edge, where the blade face from the hub to the periphery runs substantially axially, and an outflow edge, where the blade forms an angle with the axial direction which depends on the distance from the hub. In this way the most efficient vortex possible can be obtained, i.e. a vortex in which all air particles are as far as possible given the same angular speed. In this way a maximum driving couple for the rotor (the vane) is achieved. The result of the curved shape of the blades and the uniformity created in the flow pattern in the vortex downstream of the stator is in particular that no tendency to vortex formation is present either at the outflow edges of the stator blades or along the edges of the rotor. It is in fact such vortices which would make a major contribution to an increased resistance.

In the theoretically ideal case of an optimum sensitivity characteristic, a double-curved course should be selected for the blade. It has, however, been found that a very good approximation can be obtained if the device is designed in such a way that the blade face is at least partially formed by a circular cylindrical face, the central axis of said cylinder intersecting the central axis of the stator at an angle differing from 90° at such a distance that the central axis of the stator lies in a tangent plane to the cylinder.

With this shape of blade the stator is simple to cast. In this way all stators will be identical, and very good reproducibility is obtained.

The device is preferably further designed in such a way that a flat face part, passing through the central axis of the stator, connects to the circular cylindrical part of the stator face up to the inflow edge, the axial measurement of said flat face part decreasing from the hub to the peripheral edge. This provides in the first place a certain length for the connection between each blade and the hub, while the curved part of the blade need not then be directly connected to the hub. Moreover, with decreasing radial distance—where the dimension of the blade decreases in the direction of flow through the basic idea of the invention—an enlargement of the blade is achieved in that direction, so that a better inflow is obtained, and therefore a better guidance of the flow lines of the gases.

With the design ideas as described above, there are a few further dimensioning freedoms. Investigations revealed that excellent results can be obtained with a design in which the angle at which the above-mentioned central axes intersect each other is about 60°, and in that each blade takes up a sector of 45°, viewed in the axial direction of the stator. This can then also be designed in such a way that the outflow edge of each blade lies in a plane which lies a short distance from, and next to, but parallel to the central axis of the stator, that is, the central axis of the instrument. In this way, good flow properties are combined with good castability.

It is possible to strengthen the vortex while the air resistance of the instrument remains virtually the same. This is achieved in a preferred embodiment in which the stator is accommodated in a flow pipe which is initially circular cylindrical from the inflow edges of the blades and then converges towards a circular cylindrical center piece containing the rotor.

The invention will be explained below with reference to the appended drawing of a preferred embodiment.

SHORT DESCRIPTION OF THE DRAWINGS

Figure 2:
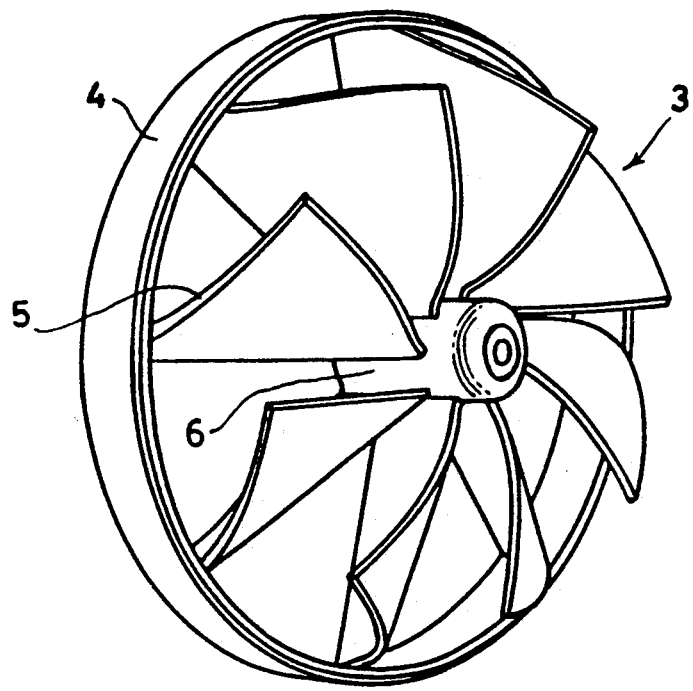
FIG. 2 shows separately in perspective a stator unit, as seen from the outflow side.

FIG. 3 gives a straight side view of the stator unit of FIG. 2; and

FIG. 4 gives a corresponding axial view from the inflow side;

FIG. 5 is a design drawing for the shape of a blade;

FIG. 6 is a view of a filter used, with a detail thereof on an enlarged scale in FIG. 6A;

FIGS. 7 and 8 illustrate how the sensor with a separate element carrying the optical means can be fixed relative to a measuring head.

DETAILED DESCRIPTION OF THE PREFERRED EMBODIMENT

Figure 1:
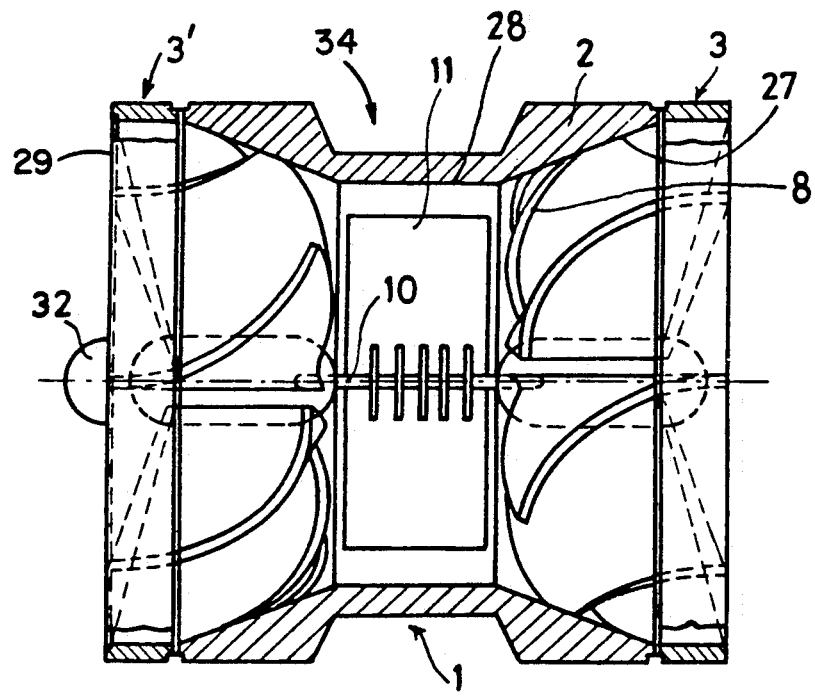
FIG. 1 shows the sensor of the flowmeter in axial cross section.

The sensor, indicated in its entirety by 1, is shown in axial cross section in FIG. 1. The housing thereof comprises a connecting piece 2 having on either side a stator unit 3, 3', the stator units being of identical design.

A stator unit 3 is shown separately in perspective in FIG. 2. It is made up of a ring 4, which forms part of the housing by being glued against the connecting piece 2, and which carries a number of blades, one of which is indicated by 5, the blades being connected at the other side to a hub 6. In the preferred embodiment of the invention eight of such blades 5 are provided. It can be seen from the axial end view of FIG. 4 that each blade 5 lies within a circle sector of 45° of the stator unit, while for the further details of the curved blades reference is made to FIGS. 3 and 5. First, however, a few comments on the terminology. For the sake of simplicity, the end edges 7 of the blades will be described as "inflow edges"; these are the edges which face the outside of the sensor unit. The edges 8 are called "outflow edges"; these are the edges facing inwards, i.e. towards the rotor. This terminology is thus correct for the stator unit which lies at the side where the gas goes into the instrument. In a particular working position these names of the end edges of the blades are interchangeable for the other stator unit. It must, however, be remembered that the instrument can operate in two directions, so that the correct names would have to be reversed again then. It is, however, felt that for the description of the shape a simplified terminology can suffice.

The ends of the individual stator blades such as 8 which are radially inward are carried by the hub 6. Prior to the further description, it is already pointed out that the whole stator as shown in FIGS. 3 and 4 in the preferred embodiment is manufactured as a single casting. The hub is therefore not a rotating part. However, the hubs of the two stator units have bearings, so that a shaft 10 is rotatable between them. The shaft 10 bears the rotor 11 which, in a manner known per se, is a flat plate, normally called a vane, which lies in an axial plane relative to the shaft 10 or the central axis 12 of the two stators and the central axis of the whole housing.

The design drawing of FIG. 5 shows a blade 5, a cross section through the peripheral ring 4, the inflow edge 7 of the blade and the outflow edge 8 thereof, and the hub 6. The inflow edge 7 is straight. Drawn through point 13, where the inflow edge 7 reaches the peripheral ring 4, is a construction line 14 which forms the central axis of an imaginary circular cylinder 15. This central axis 14 forms an angle of 30° with a construction line 16 through the point 13, at right angles to and passing through the central axis 12 of the hub. This therefore corresponds to an angle of 60° relative to the central axis 12 of the hub.

In FIG. 5 at the top a view towards the blade 5 is added, as seen along the direction of the central axis 14 of the cylinder; this central axis is indicated here by 14'. A part of the cylinder 15, indicated by 17, corresponding to a quarter of the cylinder, that is 90°, defines the shape of the curved part of blade 5 which is indicated by 18; in other words: the curved part 18 of the blade is circular cylindrical in shape. This part ends at the place which is indicated by 19 at the top of FIG. 5, while another part indicated by 20 which is flat connects tangentially thereto. The circular cylindrical part 18 of the blade is therefore bounded by the line between the points 13 and 21, in the design drawing in line with the central axis 14 of the cylinder.

The flat part 20 forms the projection of a part 22 of the blade which connects to the curved part 18 and is bounded by the straight part between the points 13 and 21, the inflow edge 7 which runs between the same point 13 and connecting point 23 on the hub 6, and then, of course, the line between the above-mentioned points 21 and 23 where the blade is connected to the hub. This flat part 22 therefore lies in an axial plane. The air arriving in the axial direction will therefore first follow this axial part 22, and the air will be deflected only from the line between the points 12 and 21 onwards.

Since the part 22 of the blade must run precisely axially and, of course, the curved part must connect uniformly thereto, in the design drawing of FIG. 5 the part 20, as already stated, run tangentially to the cylinder at the point 19. In this way it is also possible to determine where the central axis 14, 14' of the cylinder 15 is the shortest distance to the central axis 12 of the stator. This distance can be so defined that the central axis 12 of the stator lies in a tangent plane to the cylinder 15/17. The shortest distance between the two central axes 12 and 14 is thus equal to the radius of the cylinder 15/17.

It can be seen that the direction of the inflow edge 7 forms an angle of 15° with the line 16 at right angles to the central axis 12 of the hub or the stator, that is 75° relative to central axis 12. It is conceivable to make this angle slightly larger or smaller without doing away with the effect on the flow. The point 23 would thereby shift slightly to the left, or slightly to the right, in which latter case it would only be necessary for the hub 6 also to be extended slightly further to the right. In all cases the part 22 of the blade face directly behind the flow edges 7 remains extending axially.

The course of the outflow edge 8 of each blade is selected in the manner shown in FIG. 4. The design of the curved part 18 of the blade shape is simply "cut off" along a plane which from the point 24 in FIG. 4—corresponding to the projection of the connecting line between the points 21 and 23 in FIG. 5—extends parallel to the central axis 12 of the stator, at a short distance from and parallel to an imaginary plane 25 which passes through central axis 12 and centrally through the inflow edge 7 of the succeeding blade so a radial plane). With this selection, a suitable uniform rate distribution is achieved at the side of the outflow edge if two other parameters, namely the sector angle of 45° within which each blade 5 lies (so that there are eight blades) and the angle of approximately 30° between the lines 14 and 16, correspond, as already said, to approximately 60° between the cylinder central axis 14 and the central axis 12 of the stator.

It is conceivable for the flow pipe which is formed by the interior of the housing to be fully circular cylindrical. In that case the blade simply extends—on the design principles described with reference to FIG. 5—right through to the outside up to the cylindrical inside wall of the flow pipe. In the preferred embodiment of the invention this flow pipe is, however, given a certain convergence. While the interior of the ring 3 of the stator unit is cylindrical, the flow pipe converges thereafter, as indicated by 27 in FIG. 2. It can also be seen from FIG. 1 that this convergent part 27 of the flow pipe essentially extends as far as the outflow edges 8 of the blades. By this convergence a strengthening of the vortex is achieved, producing an increase in the rate of flow of the gases at the outflow edges of the blades, while the air resistance of the instrument as a whole remains virtually unchanged. In any case this applies to the dimension ratios drawn to scale in which the diameter of the flow pipe in the convergent piece 27 is reduced to about 20%. This implies a narrowing of the surface of the flow cross section to just over 60%.

The principles described for shaping the blades mean that the gas particles are being given as far as possible the same angular velocity at all radial distances. In this way a maximum driving couple on the vane is produced.

As a result of the reproducibility of its sensitivity characteristic, the instrument can be used in both positions. However, insofar as the flowmeter is used in equipment for the analysis of breathing air, it is advisable to provide a filter at the air infeed side. FIGS. 6 and 6a show a preferred embodiment of such a filter. It comprises a disc which is indicated in its entirety by 29. With the exception of an area 30 along the periphery and a central area 31, it is provided with a pattern of holes which is shown enlarged in FIG. 6a. For this, according to the invention a honeycomb pattern is chosen because with this, contrary to the case where a pattern of circular openings is used, the smallest air resistance is achieved. For practical use it has been found beneficial if the dimension d1 of the hexagonal holes is approximately 1 mm and the dimension d2 of the material between adjacent holes is approximately 0.25 mm. Another advantage of this filter is that it considerably improves the uniformity in the air flow at the infeed side of the sensor. This is important because in various applications the sensor is a very short distance from the person's mouth, and because breathing air in the nature of things can produce a great vortex at high air velocities.

The filter 29 is shown with a broken line in FIG. 1, together with a pin 32 by means of which it can be fixed in an aperture in the end of the hub 9.

The embodiment described has a dynamic range of 1:1000.

The fact that in the interior of the sensor housing 2 the converging parts 27 having a smaller cross section of the part 28 where the rotor is located provides an interesting new possibility. If, as is shown in FIG. 1, the housing 2 of the sensor also externally has a central part 34 having a reduced diameter, the sensor can be fitted in a measuring head 35 having a design as shown in FIGS. 7 and 8. The head 35 is essentially cylindrical, so that the sensor unit 1 can be inserted into it in the direction of arrow P1 in FIG. 7. The all of the head 35 is provided with a recess 36 in the form of a circle sector—in the embodiment shown approximately 180°—but it can also be smaller. Into it fits a loose part 37 which is shaped like a circle sector and has at least a light source, indicated by 38, and a cell, indicated by 39, of the optical system with which the revolutions of the rotor are counted, and which can be connected by means of a cable 40 to the remaining electronics of the device.

As can be seen from FIG. 8, the radial dimension of this loose piece 37 is greater than the wall thickness of the head 35, so that the part 37 then projects further inwards, up to the point of the narrowed central part 34 of the sensor unit 1. When the part 37 is removed, the sensor unit can be taken out of the head while, conversely, after axial sliding in of the sensor unit 1 into the head 35 in the direction of arrow P1 and subsequent placing of the part 37 in the radial direction according to the arrow P2, the sensor unit 1 is secured.

As a measure for securing the circle sector-shaped loose part 37 relative to the head 35, the invention provides the following design solution. A part 41 of the head is designed as a ring which with screw thread 42 is rotatable relative to the part 43 which still remains within the radial dimension of the head. The screw ring is provided on the side facing the recess 36 with a rib 44 over a part of the periphery, while the part 37 is provided with a corresponding groove 45 (compare also FIG. 7). If the rib 44 is in the hollow of the recess 36, it will engage in the groove 45 insofar as the part 37 is inserted there. Loosening the ring 38 a half turn will move the rib 44 outside the recess, so that part 37 is released and can be removed in the direction opposite to that of the arrow P2 in FIG. 7.

What is claimed is:

1. A flowmeter for gases, comprising a sensor having a housing which is open at two opposite ends for the infeed and discharge of the gases to be measured, and in which a rotor is rotatable about an axis between two stators which are substantially at right angles to the said axis and which comprise deflection blades, while optical means are provided to detect the rotation of the rotor and convert it into an electrical output signal, wherein each of the stator deflection blades is curved between an inflow edge, where the blade from the hub to the periphery extends substantially in an axial plane, and an outflow edge, where the blade surface at each point thereof forms an angle with the axial direction which angle varies with the distance of each said point from the hub.

2. A flowmeter as in claim 1, wherein the blade surface is at least partially formed by part of a circular cylindrical surface, the central axis of said cylinder and the central axis of the stator being at an angle differing from 90° and the central axis of the stator lying in a tangent plane to the cylinder.

3. A flowmeter as in claim 2 wherein a flat face part of the stator, passing through the central axis thereof, connects to the circular cylindrical part of the stator face up to the inflow edge, the axial dimension of said flat face part decreasing from the hub to the peripheral edge.

4. A flowmeter as in claim 3 wherein the angle between said central axes of said cylinder and said stator is about 60°, each blade taking up a sector of 45°, viewed in the axial direction of the stator.

5. A flowmeter as in claim 3 wherein the inflow edge lies in a radial plane of the stator at an angle of approximately 75° relative to the central axis.

6. A flowmeter as in claim 1 wherein the stator is accommodated in a flow pipe which comprises circular cylindrical parts near the inflow edges of the blades and then converges towards a circular cylindrical center piece containing the rotor.

7. A flowmeter as in claim 1 wherein the blades and the hub forming the stator are manufactured as a separate casting with an annular peripheral part of the housing.

8. A flowmeter as in claim 6 wherein a connecting piece of the housing is formed by said circular cylindrical center piece with the two convergent parts, to which the annular peripheral parts of the stators are fixed in a close-fitting manner.

9. A flowmeter as in claim 1 wherein the outflow edge of the blade lies parallel to but displaced from an axial plane through the central axis of the stator.

10. A flowmeter as in claim 6 wherein the housing of the sensor also comprises externally a center piece having a reduced diameter, and this sensor being fitted in a holder or head which is provided with a circle sector-shaped recess in a wall thereof into which a separate, also circle sector-shaped part can be inserted, which carries parts of the optical system, and having a radial dimension which is greater than the wall thickness of the holder or head, such that this part comes to rest at the center piece of the housing of the sensor and thereby blocks axial displacement of the sensor relative to the housing or head.

11. A flowmeter as in claim 10 wherein said circular piece is retained relative to the housing or the head by a screw ring which is provided with a rib which mates with a groove in said circle-shaped part.

* * * * *